(12) United States Patent
Rust et al.

(10) Patent No.: US 11,020,223 B2
(45) Date of Patent: *Jun. 1, 2021

(54) TRANSCATHETER DELIVERY SYSTEM AND METHOD WITH CONTROLLED EXPANSION AND CONTRACTION OF PROSTHETIC HEART VALVE

(71) Applicant: Medtronic, Inc., Minneapolis, MN (US)

(72) Inventors: Matthew Rust, Windsor, CA (US); Savage Padraig, Santa Rosa, CA (US); Gianfranco Pellegrini, Santa Rosa, CA (US); Finn Rinne, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 582 days.

This patent is subject to a terminal disclaimer.

(21) Appl. No.: 15/387,071

(22) Filed: Dec. 21, 2016

(65) Prior Publication Data

US 2017/0100246 A1 Apr. 13, 2017

Related U.S. Application Data

(63) Continuation of application No. 13/149,160, filed on May 31, 2011, now Pat. No. 9,561,102.
(Continued)

(51) Int. Cl.
*A61F 2/24* (2006.01)
*A61F 2/95* (2013.01)
*A61F 2/966* (2013.01)

(52) U.S. Cl.
CPC .......... *A61F 2/2436* (2013.01); *A61F 2/2418* (2013.01); *A61F 2/2427* (2013.01);
(Continued)

(58) Field of Classification Search
None
See application file for complete search history.

(56) References Cited

U.S. PATENT DOCUMENTS 5,480,423 A 1/1996 Ravenscroft et al.
5,683,451 A 11/1997 Lenker et al.
(Continued)

FOREIGN PATENT DOCUMENTS

EP 1982677 10/2008
GB 2433700 7/2007
(Continued)

*Primary Examiner* — Shaun L David
(74) *Attorney, Agent, or Firm* — Dicke, Billig & Czaja, PLLC

(57) ABSTRACT

A delivery system for use with a prosthetic heart valve having a stent frame to which a valve structure is attached, includes a shaft assembly including a distal end and a coupling structure disposed near the distal end and configured to be coupled to a distal end of the prosthetic heart valve. The system includes a sheath assembly defining a lumen sized to slidably receive the shaft assembly. The delivery system is configured to transition from a loaded state in which the sheath assembly encompasses the prosthetic heart valve to a deployed state in which the sheath assembly is withdrawn from the prosthetic heart valve. The coupling structure is configured to provide a controlled expansion or contraction of the distal end of the prosthetic heart valve based on longitudinal movement of the distal end of the shaft assembly.

19 Claims, 11 Drawing Sheets

Related U.S. Application Data

(60) Provisional application No. 61/350,656, filed on Jun. 2, 2010.

(52) U.S. Cl.
CPC ..... *A61F 2/2439* (2013.01); *A61F 2002/9505* (2013.01); *A61F 2002/9665* (2013.01); *A61F 2230/005* (2013.01); *A61F 2230/008* (2013.01); *A61F 2230/0054* (2013.01)

(56) References Cited

U.S. PATENT DOCUMENTS

| | | | |
|---|---|---|---|
| 5,693,083 A | 12/1997 | Baker et al. | |
| 5,824,041 A | 10/1998 | Lenker et al. | |
| 5,906,619 A | 5/1999 | Olson et al. | |
| 5,957,949 A | 9/1999 | Leonhardt et al. | |
| 6,248,128 B1 | 6/2001 | Berry et al. | |
| 7,105,016 B2 | 9/2006 | Shiu et al. | |
| 2003/0050694 A1 | 3/2003 | Yang et al. | |
| 2003/0199963 A1 | 10/2003 | Tower et al. | |
| 2005/0137688 A1 | 6/2005 | Salahieh et al. | |
| 2005/0288763 A1 | 12/2005 | Andreas et al. | |
| 2006/0004439 A1 | 1/2006 | Spenser et al. | |
| 2006/0052867 A1 | 3/2006 | Revuelta et al. | |
| 2006/0229561 A1 | 10/2006 | Huszar | |
| 2006/0259136 A1 | 11/2006 | Nguyen et al. | |
| 2006/0265056 A1 | 11/2006 | Nguyen et al. | |
| 2007/0005131 A1 | 1/2007 | Tyalor | |
| 2007/0088431 A1 | 4/2007 | Bourang et al. | |
| 2007/0239266 A1 | 10/2007 | Birdsall | |
| 2007/0239269 A1 | 10/2007 | Dolan et al. | |
| 2008/0065011 A1 | 3/2008 | Marchand et al. | |
| 2008/0082165 A1 | 4/2008 | Wilson et al. | |
| 2008/0132989 A1* | 6/2008 | Snow | A61F 2/966 623/1.12 |
| 2008/0147160 A1 | 6/2008 | Ghione et al. | |
| 2008/0147181 A1 | 6/2008 | Ghione et al. | |
| 2008/0188928 A1 | 8/2008 | Salahieh et al. | |
| 2008/0262590 A1 | 10/2008 | Murray | |
| 2009/0093876 A1 | 4/2009 | Nitzan et al. | |
| 2009/0138079 A1 | 5/2009 | Tuval et al. | |
| 2009/0171447 A1 | 7/2009 | Von Segesser et al. | |
| 2009/0177275 A1 | 7/2009 | Case | |
| 2009/0182405 A1 | 7/2009 | Arnault et al. | |
| 2009/0228093 A1* | 9/2009 | Taylor | A61F 2/2418 623/1.12 |
| 2009/0281619 A1 | 11/2009 | Le et al. | |
| 2010/0049313 A1 | 2/2010 | Alon et al. | |
| 2010/0094411 A1 | 4/2010 | Tuval et al. | |
| 2010/0121434 A1 | 5/2010 | Paul et al. | |
| 2011/0178588 A1 | 7/2011 | Haselby | |

FOREIGN PATENT DOCUMENTS

| | | |
|---|---|---|
| WO | WO2008138584 | 11/2008 |
| WO | WO2008091509 | 7/2009 |
| WO | WO 2010027485 | 3/2010 |
| WO | WO 2010044874 | 4/2010 |

\* cited by examiner

TRANSCATHETER DELIVERY SYSTEM AND METHOD WITH CONTROLLED EXPANSION AND CONTRACTION OF PROSTHETIC HEART VALVE

CROSS-REFERENCE TO RELATED APPLICATIONS

This application is a Continuation of and claims priority to U.S. patent application Ser. No. 13/149,160, filed May 31, 2011, issued as U.S. Pat. No. 9,561,102 B2 on Feb. 7, 2017, which claims priority under 35 U.S.C. § 119(e)(1) to U.S. Provisional Patent Application Ser. No. 61/350,656, filed Jun. 2, 2010, the entire disclosures of which are incorporated herein by reference.

BACKGROUND

The present disclosure relates to systems and methods for percutaneous implantation of a heart valve prosthesis. More particularly, it relates to delivery systems and methods for transcatheter implantation of a stented prosthetic heart valve.

Heart valves, such as the mitral, tricuspid, aortic, and pulmonary valves, are sometimes damaged by disease or by aging, resulting in problems with the proper functioning of the valve. Heart valve problems generally take one of two forms: stenosis in which a valve does not open completely or the opening is too small, resulting in restricted blood flow; or insufficiency in which blood leaks backward across a valve when it should be closed.

Heart valve replacement has become a routine surgical procedure for patients suffering from valve regurgitation or stenotic calcification of the leaflets. Conventionally, the vast majority of valve replacements entail full sternotomy in placing the patient on cardiopulmonary bypass. Traditional open surgery inflicts significant patient trauma and discomfort, requires extensive recuperation times, and may result in life-threatening complications.

To address these concerns, within the last decade, efforts have been made to perform cardiac valve replacements using minimally-invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery of replacement cardiac valves to solve the problems presented by traditional open surgery and minimally-invasive surgical methods. In such methods, a valve prosthesis is compacted for delivery in a catheter and then advanced, for example through an opening in the femoral artery and through the descending aorta to the heart, where the prosthesis is then deployed in the valve annulus (e.g., the aortic valve annulus).

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, prosthetic heart valve designs attempt to replicate the function of the valve being replaced and thus will include valve leaflet-like structures used with either bioprostheses or mechanical heart valve prostheses. If bioprostheses are selected, the replacement valves may include a valved vein segment or pericardial manufactured tissue valve that is mounted in some manner within an expandable stent frame to make a valved stent. In order to prepare such a valve for percutaneous implantation, one type of valved stent can be initially provided in an expanded or uncrimped condition, then crimped or compressed around a balloon portion of a catheter until it is close to the diameter of the catheter. In other percutaneous implantation systems, the stent frame of the valved stent can be made of a self-expanding material. With these systems, the valved stent is crimped down to a desired size and held in that compressed state with a sheath, for example. Retracting the sheath from this valved stent allows the stent to expand to a larger diameter, such as when the valved stent is in a desired position within a patient. With either of these types of percutaneous stent delivery systems, conventional sewing of the prosthetic heart valve to the patient's native tissue is typically not necessary.

It is imperative that the stented heart valve prosthesis be accurately located relative to the native annulus prior to full deployment from the catheter. Successful implantation requires that the transcatheter prosthetic heart valve intimately lodge and seal against the native annulus. A self-expanding transcatheter heart valve must have a high radial force when expanding to properly anchor itself in the anatomy of the heart. If the prosthetic is incorrectly positioned relative to the native annulus, serious complications can result as the deployed device will leak and even may dislodge from the implantation site. Greatly complicating this effort is the fact that once the heart valve prosthesis (e.g., a self-deploying stent) is deployed from the catheter, it is exceedingly difficult to re-collapse or "recapture" the prosthetic with conventional delivery tools (e.g., an outer sheath or catheter). This same concern does not arise in the context of other vascular stents; with these procedures, if the target site was "missed," another stent is simply deployed to "make-up" the difference.

While imaging technology can be employed as part of the implantation procedure to assist a clinician in better evaluating a location of the transcatheter prosthetic heart valve immediately prior to deployment, in many instances, this evaluation alone is insufficient. Instead, clinicians desire the ability to partially deploy the prosthesis and then evaluate a position relative to the native annulus prior to full deployment. While in theory the "re-capturing" of a partially deployed stented prosthetic heart valve is straight forward, in actual practice, the constraints presented by the implantation site and the stented heart valve itself render the technique exceedingly difficult.

In light of the above, although there have been advances in percutaneous valve replacement techniques and devices, there is a continued desired to provide different delivery systems for delivering and repositioning cardiac replacement valves, and in particular self-expanding stented prosthetic heart valves, to an implantation site in a minimally invasive and percutaneous manner. There is also a continuing desire to be able to provide a more controlled deployment of replacement valves, and to be able to reposition and/or retract the valves once they have been deployed or partially deployed in order to ensure optimal placement of the valves within the patient.

SUMMARY

One embodiment is directed to a delivery system for use with a prosthetic heart valve having a stent frame to which a valve structure is attached. The system includes a shaft assembly including a distal end and a coupling structure disposed near the distal end and configured to be coupled to a distal end of the prosthetic heart valve. The system includes a sheath assembly defining a lumen sized to slidably receive the shaft assembly. The delivery system is configured to transition from a loaded state in which the sheath assembly encompasses the prosthetic heart valve to a deployed state in which the sheath assembly is withdrawn from the prosthetic heart valve. The coupling structure is configured to provide a controlled expansion or contraction of the distal end of the prosthetic heart valve based on longitudinal movement of the distal end of the shaft assembly.

Another embodiment is directed to a system for performing a therapeutic procedure on a defective heart valve of a patient. The system includes a delivery system including a shaft assembly with a distal end and a coupling structure disposed near the distal end and configured to be coupled to a distal end of the prosthetic heart valve. The delivery system includes a sheath assembly defining a lumen sized to slidably receive the shaft assembly. The system includes a prosthetic heart valve having a stent frame and a valve structure attached to the stent frame and forming at least two valve leaflets. The prosthetic heart valve is self-expandable from a compressed arrangement to a natural arrangement. The delivery system is configured to slidably receive the prosthetic heart valve within the sheath assembly and is configured to be operable to transition from a loaded state in which the sheath assembly encompasses the prosthetic heart valve to a deployed state in which the sheath assembly is withdrawn from the prosthetic heart valve to permit the prosthetic heart valve to self-expand to the natural arrangement and release from the delivery system. The coupling structure is configured to provide a controlled expansion of the distal end of the prosthetic heart valve based on longitudinal movement of the distal end of the shaft assembly in a first direction, and provide a controlled contraction of the distal end of the prosthetic heart valve based on longitudinal movement of the distal end of the shaft assembly in a second direction opposite to the first direction.

Yet another embodiment is directed to a method of performing a therapeutic procedure on a defective heart valve of a patient. The method includes receiving a delivery system loaded with a self-expanding prosthetic heart valve having a stent frame to which a valve structure is attached. The delivery system includes a shaft assembly slidably positioned within a delivery sheath. The shaft assembly includes a coupling structure disposed near a distal end of the shaft assembly and coupled to a distal end of the prosthetic heart valve. The delivery sheath contains the prosthetic heart valve in a compressed arrangement. The method includes manipulating the delivery system to guide the prosthetic heart valve through the patient's vasculature and into the defective heart valve, and withdrawing the delivery sheath from the prosthetic heart valve. The distal end of the shaft assembly is moved in a first longitudinal direction to cause the coupling structure to provide a controlled expansion of the distal end of the prosthetic heart valve, and the prosthetic heart valve is released from the delivery system.

DETAILED DESCRIPTION

Figure 1A:
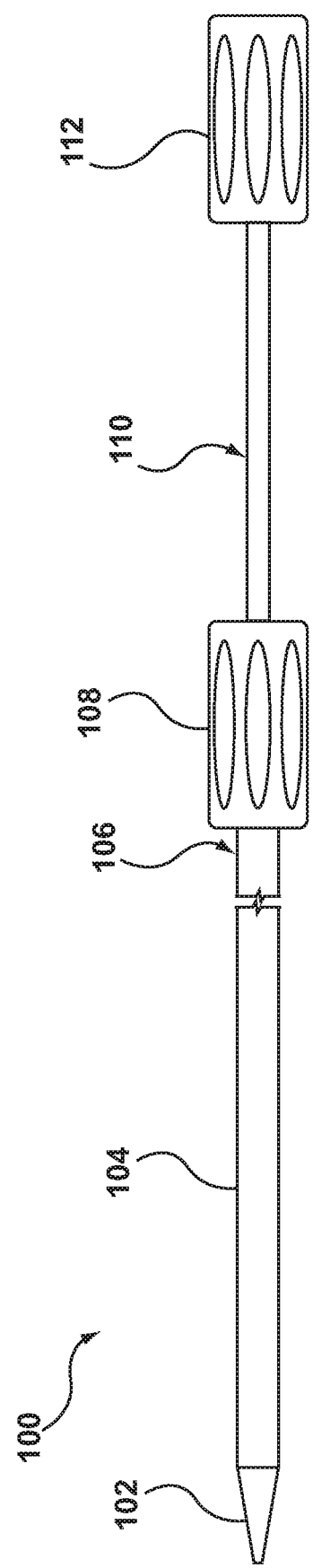
FIGS. 1A-1D are diagrams illustrating a system for delivering a transcatheter prosthetic heart valve to an implantation site according to one embodiment.

The terms "distal" and "proximal" are used herein with reference to the treating clinician during the use of the catheter system; "Distal" indicates an apparatus portion distant from, or a direction away from the clinician and "proximal" indicates an apparatus portion near to, or a direction towards the clinician. The term "therapy" or "therapeutic procedure" as used herein in the context of heart valves is intended to include the repair of a heart valve, the replacement of a heart valve, or a combination of repair and replacement of a heart valve. While some of the description herein may refer specifically to therapy of aortic valves, the systems and methods disclosed herein can also generally be used for therapy of native or bioprosthetic mitral, pulmonic, or tricuspid valves.

FIGS. 1A-1D are diagrams illustrating a system 100 for delivering a transcatheter prosthetic heart valve to an implantation site according to one embodiment. In the illustrated embodiment, the system 100 includes a shaft assembly 110 and a sheath assembly 106. The shaft assembly 110 includes a handle device 112, a carrier shaft 120, a connector shaft 115, a nose cone 102, and a coupling structure 122. The connector shaft 115 interconnects the carrier shaft 120 and the nose cone 102, and in some constructions has a reduced-sized diameter to permit placement of a prosthetic heart valve 114 over the connector shaft 115. In one embodiment, shafts 115 and 120 are independently controllable via the handle device 112. The nose cone 102 is disposed at the distal end of the shaft assembly 110. Though not shown in FIGS. 1A-1D, a guide wire lumen can be formed through the shafts 115 and 120. In one embodiment, shaft 115 is a guide wire shaft that defines the guide wire lumen.

Carrier shaft 120 is sized to be slidably received within the sheath assembly 106, and is configured in the illustrated embodiment for releasable coupling with the prosthetic heart valve 114. The carrier shaft 120 forms or includes a coupling device 117. The coupling device 117 is configured to selectively retain a proximal portion of the prosthetic heart valve 114. The coupling device 117 is configured to releasably mount the prosthetic heart valve 114 to the shaft assembly 110 when the prosthetic heart valve 114 is forced to a collapsed state within the sheath assembly 106. In this collapsed state, then, the prosthetic heart valve 114 will longitudinally move with movement of the shaft assembly 110. The sheath assembly 106 is configured to permit deployment of the prosthetic heart valve 114 from the loaded state shown in FIGS. 1A and 1B. The delivery system 100 is configured to transition from the loaded state in which the sheath assembly 106 encompasses the prosthetic heart valve 114 to a deployed state in which the sheath assembly 106 is withdrawn from the prosthetic heart valve 114.

The coupling structure 122 is disposed near the distal end of the shaft assembly 110. The coupling structure 122 is attached (e.g., bonded) to a proximal end of the nose cone 102, and extends proximally from the proximal end of the nose cone 102 toward the prosthetic heart valve 114. In the illustrated embodiment, the coupling structure 122 includes a tubular base portion 124, and a plurality of legs 126 that extend away from the base portion 124. The distal end of the prosthetic heart valve 114 is releasably coupled to the legs 126 of the coupling structure 122. The coupling structure 126 is configured to move distally and proximally with a corresponding movement of the nose cone 102 to provide a controlled expansion and contraction of the distal end of the prosthetic heart valve 114. Thus, the coupling structure 122 according to one embodiment provides the controlled expansion or contraction based on longitudinal movement of the distal end of the shaft assembly 110 and the nose cone 102. In one embodiment, a clinician pushes or pulls the shaft 115 (e.g., via handle device 112), which causes a corresponding longitudinal movement of the nose cone 102, including the coupling structure 122.

The nose cone 102 can assume a variety of forms, and is generally constructed to facilitate atraumatic placement of the delivery system 100 through a patient's vasculature and heart. The handle device 112 is mounted or connected to a proximal end of the carrier shaft 120, and provides a convenient surface for grasping by a clinician.

The sheath assembly 106 generally includes a sheath 104 and a handle device 108. The sheath 104 can be of a conventional catheter-like configuration (e.g., biocompatible polymer with or without an encapsulated wire braiding). In some constructions, the sheath 104 can further incorporate various steering features. Regardless, the sheath 104 is generally compliant, and is able to traverse the tortuous pathways associated with transcatheter heart valve implantation. The handle device 108 can assume a wide variety of forms, and is generally mounted or connected to a proximal end of the sheath 104. The sheath 104 defines a lumen sized to slidably receive the carrier shaft 120, as well as the prosthetic heart valve 114 in the collapsed state.

Figure 1B:
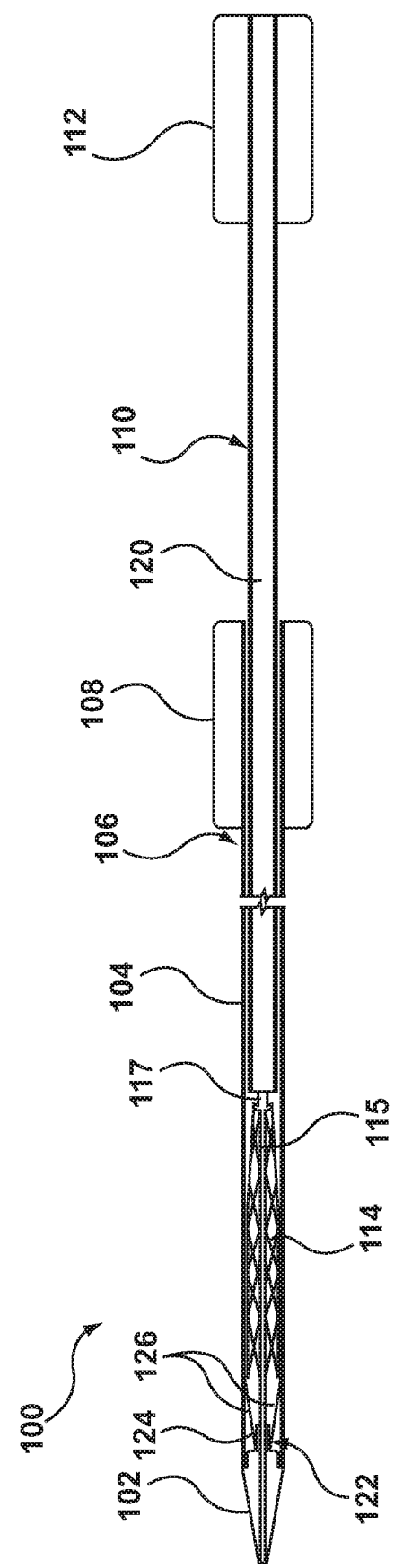

The delivery system 100 is operable to deliver or implant the prosthetic heart valve 114 as described in further detail below. FIGS. 1A and 1B illustrate the system 100 loaded with the prosthetic heart valve 114 prior to deployment. In particular, the prosthetic heart valve 114 is connected to the carrier shaft 120, for example via the coupling device 117, and is radially constrained within the sheath 104. The delivery system 100 is configured to be operable to transition from a loaded state in which the sheath 104 encompasses the prosthetic heart valve 114 to a deployed state in which the sheath 104 is withdrawn from the prosthetic heart valve 114 to permit the prosthetic heart valve 114 to self-expand to a natural arrangement and release from the delivery system 100, as described in further detail below.

Figure 1C:
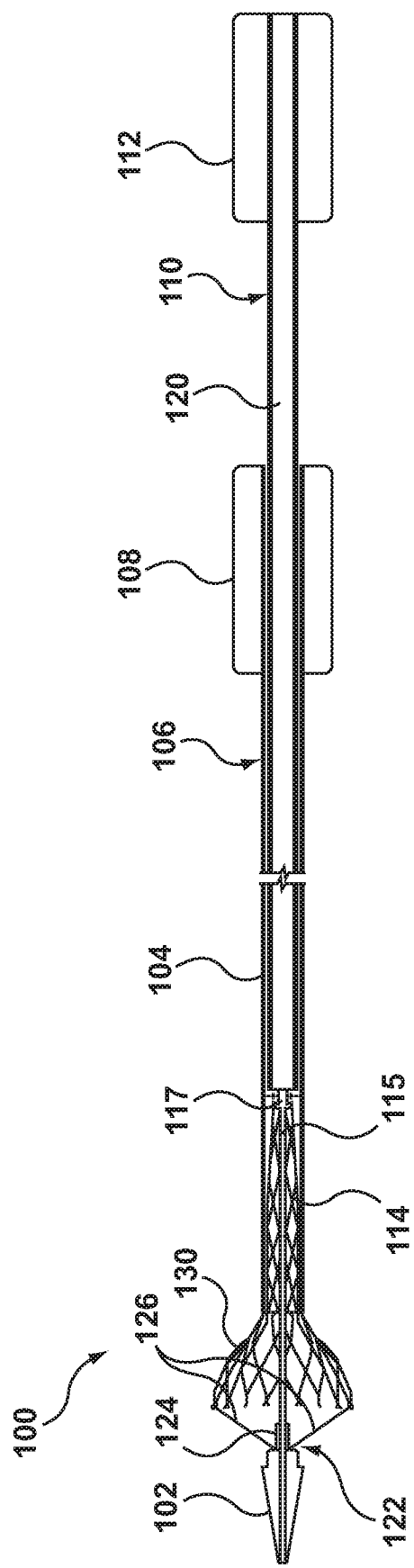

The loaded delivery system 100 is advanced toward the implantation target site, for example in a retrograde manner through a cut-down to the femoral artery and into the patient's descending aorta. The delivery system 100 is then advanced, under fluoroscopic guidance, over the aortic arch, through the ascending aorta, and midway across the defective aortic valve (for aortic replacement). After positioning of the delivery system 100, the sheath 104 is partially retracted relative to the prosthetic heart valve 114 as shown in FIG. 1C. For example, the handle device 108 provided with the sheath assembly 106 is retracted toward the handle device 112 of the shaft assembly 110. As shown, a distal region 130 of the prosthetic heart valve 114 is thus exteriorly exposed relative to the sheath 104, and begins to self-expand and self-deploy. However, the self-expansion of the distal region 130 of the prosthetic heart valve 114 is controllably restrained in one embodiment by coupling structure 122. The prosthetic heart valve 114 is allowed to gradually self-expand by moving coupling structure 122 in a first longitudinal direction (e.g., in a proximal direction) via the handle device 112. As the coupling structure 122 is moved in the first direction, the coupling structure 122 moves closer to the prosthetic heart valve 114, resulting in the coupling structure 122 applying less compressive force to the prosthetic heart valve 114 and allowing the distal end of the valve 114 to self-expand. FIG. 1C shows the delivery system 100 after the coupling structure 122 has been moved in the proximal direction to provide a controlled expansion of the valve 114.

This proximal retraction of the sheath 104 and controlled expansion of the prosthetic heart valve 114 continues, with a continually increasing length of the prosthetic heart valve 114 being exposed and thus partially deployed, until the prosthetic heart valve 114 is fully deployed at the native heart valve. In one embodiment, continued movement of the coupling structure 122 in the first direction causes the legs 126 to eventually slide off the distal end of the prosthetic heart valve 114 and thereby release the valve 114. Thus, the coupling structure 122 according to one embodiment is configured to be automatically released from the distal end of the prosthetic heart valve 114 when the prosthetic heart valve 114 expands beyond a threshold amount. After deployment, the nose cone 102 and the coupling structure 122 are pulled back through the deployed valve 114, and the delivery system 100 is removed from the patient.

Prior to full deployment, the position of the prosthetic heart valve 114 relative to the implant site may also be evaluated when it is in a partially deployed state, such as that shown in FIG. 1C. In the event the clinician believes, based upon the above evaluation, that the prosthetic heart valve 114 should be repositioned relative to the implant site, the prosthetic heart valve 114 is first contracted or "resheathed".

Figure 1D:
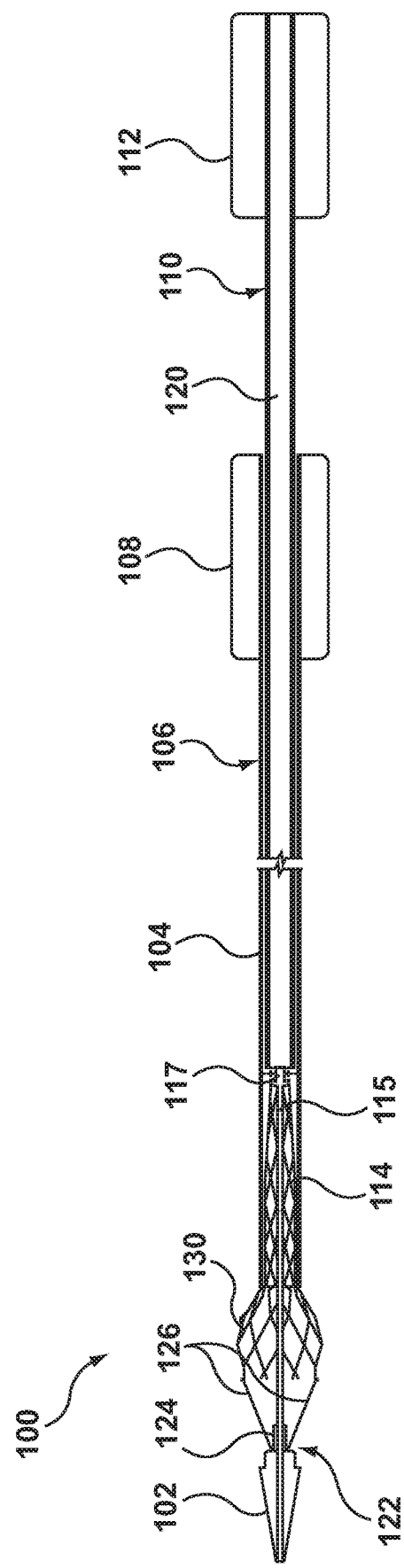

The resheathing process according to one embodiment involves moving coupling structure 122 in a second longitudinal direction (e.g., in a distal direction) opposite the first direction via the handle device 112. As the coupling structure 122 is moved in the second direction, the coupling structure 122 moves farther away from the prosthetic heart valve 114, resulting in the coupling structure 122 applying more compressive force to the prosthetic heart valve 114, and causing a controlled contraction of the distal end of the valve 114. The sheath 104 is then advanced distally relative to the shaft assembly 110, and thus relative to the prosthetic heart valve 114. Distal movement of the sheath 104 continues until the prosthetic heart valve 114 is fully resheathed within the sheath 104. The controlled contraction of the distal end of the prosthetic heart valve 114 by coupling structure 122 reduces the force required for the resheathing of the valve 114. FIG. 1D shows the delivery system 100 after the coupling structure 122 has been moved in the distal direction to provide a controlled contraction of the valve 114. Once the prosthetic heart valve 114 is resheathed or recaptured, the system 100 can be repositioned relative to the implantation site, and the process repeated until the clinician is comfortable with the achieved positioning. Alternatively, the resheathed prosthetic heart valve 114 can be removed from the patient. The prosthetic heart valve 114 may also be repositioned without being completely resheathed.

The delivery system 100 is useful with a variety of different configurations of a stented prosthetic heart valve. In general terms, the prosthetic heart valve 114 includes a stent frame maintaining a valve structure (tissue or synthetic), with the stent frame having a normal, expanded state and collapsible to a collapsed state for loading within the system 100. The stent frame can be constructed to self-deploy or self-expand when released from the delivery system 100, or a separate expansion member can be provided (e.g., an expansion balloon). For example, the prosthetic heart valve 114 can be a prosthetic sold under the trade name CoreValve® available from Medtronic CoreValve, LLC. Other non-limiting examples of transcatheter heart valve prostheses useful with the system 100 are described in U.S. Publication Nos. 2006/0265056; 2007/0239266; and 2007/0239269; the teachings of each of which are incorporated herein by reference.

Figure 2A:
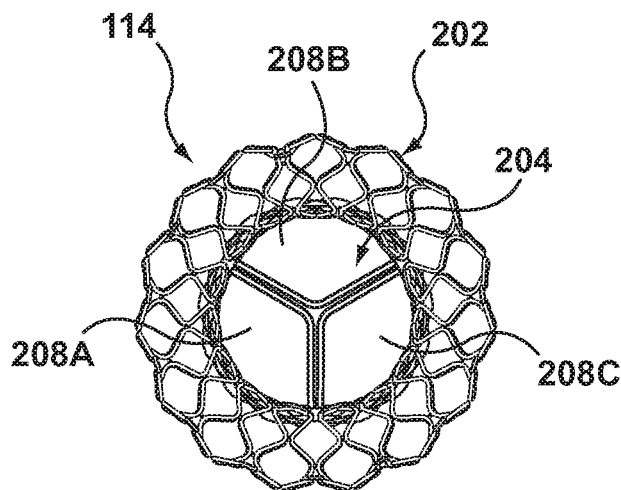
FIGS. 2A-2C are diagrams illustrating one embodiment of the prosthetic heart valve shown in FIGS. 1B-1D.
Figure 2B:
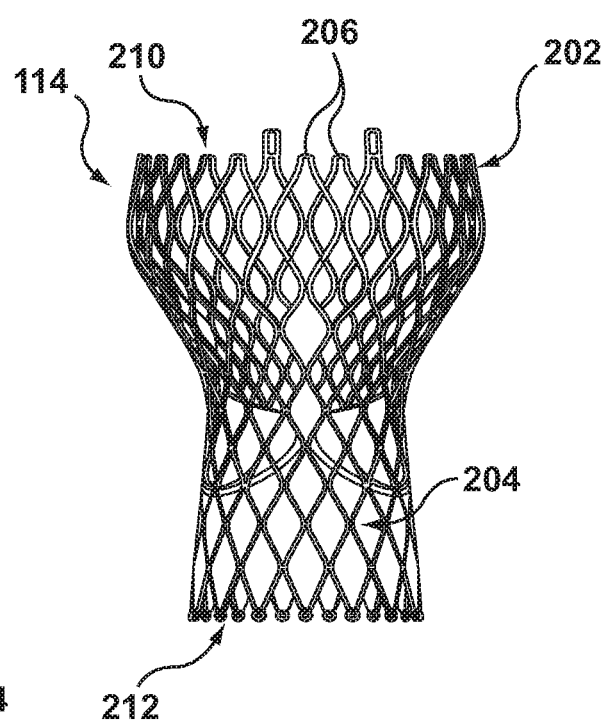
Figure 2C:
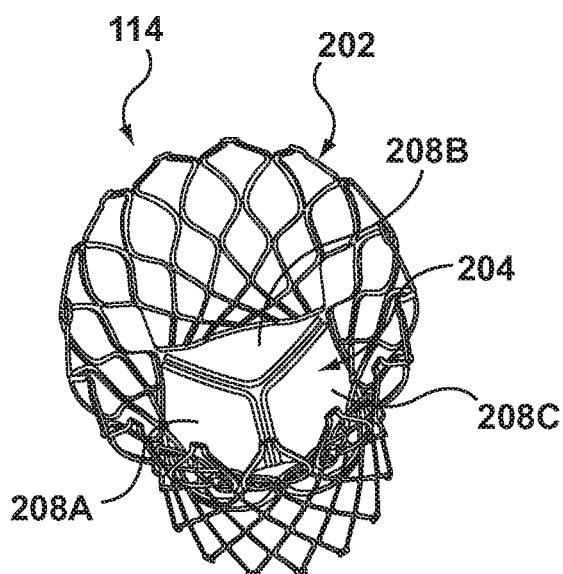

FIG. 2A is a diagram illustrating a top view of one embodiment of the prosthetic heart valve 114 shown in FIGS. 1B-1D. FIG. 2B is a diagram illustrating a side view of the prosthetic heart valve 114 shown in FIG. 2A according to one embodiment. FIG. 2C is a diagram illustrating a perspective view of the prosthetic heart valve 114 shown in FIG. 2A according to one embodiment. Prosthetic heart valve 114 is compressible to a relatively small diameter for percutaneous delivery to the heart of a patient, and is then self-expandable via removal of external compressive forces. Prosthetic heart valve 114 according to one embodiment is self-expandable from a compressed arrangement to a natural arrangement As shown in FIGS. 2A-2C, prosthetic heart valve 114 includes a stent frame 202 and a valve structure 204. The stent frame 202 is a self-expanding support structure that includes a number of strut or wire portions 206 arranged relative to each other to provide a desired compressibility and strength to the prosthetic heart valve 114. Stent frame 202 can be made from a shape memory material, such as Nitinol. Valve structure 204 is mounted inside of the stent frame 202, and includes a plurality of leaflets 208A-208C (collectively referred to as leaflets 208). In the illustrated embodiment, valve structure 204 includes three leaflets 208. In other embodiments, valve structure 204 may include more or less than three leaflets 208. FIG. 2B also shows a proximal outflow end 210 and a distal inflow end 212 of prosthetic heart valve 114.

Figure 3A:
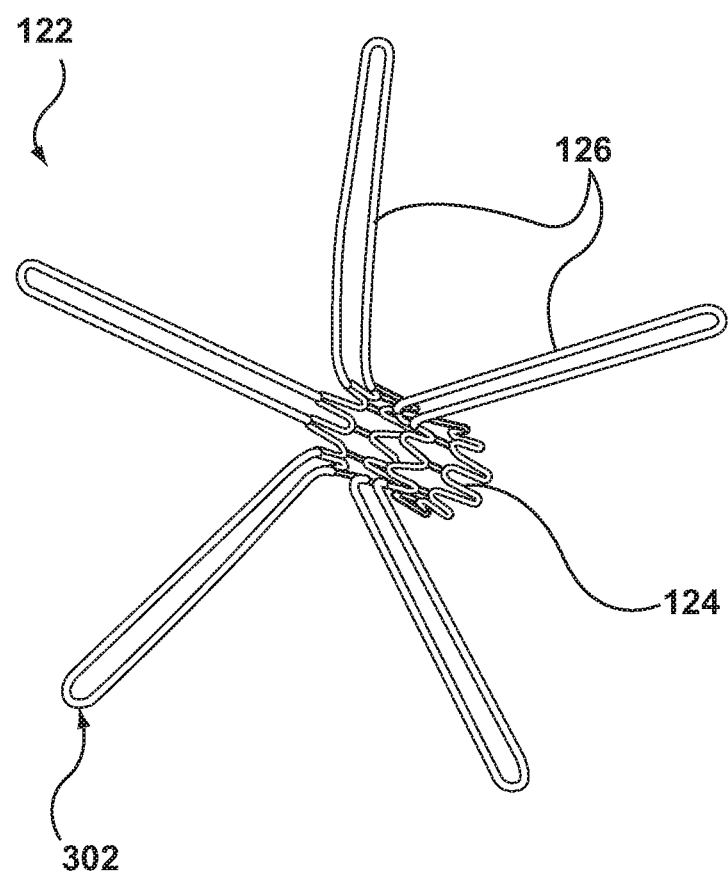
FIGS. 3A and 3B are images illustrating a coupling structure according to one embodiment.
Figure 3B:
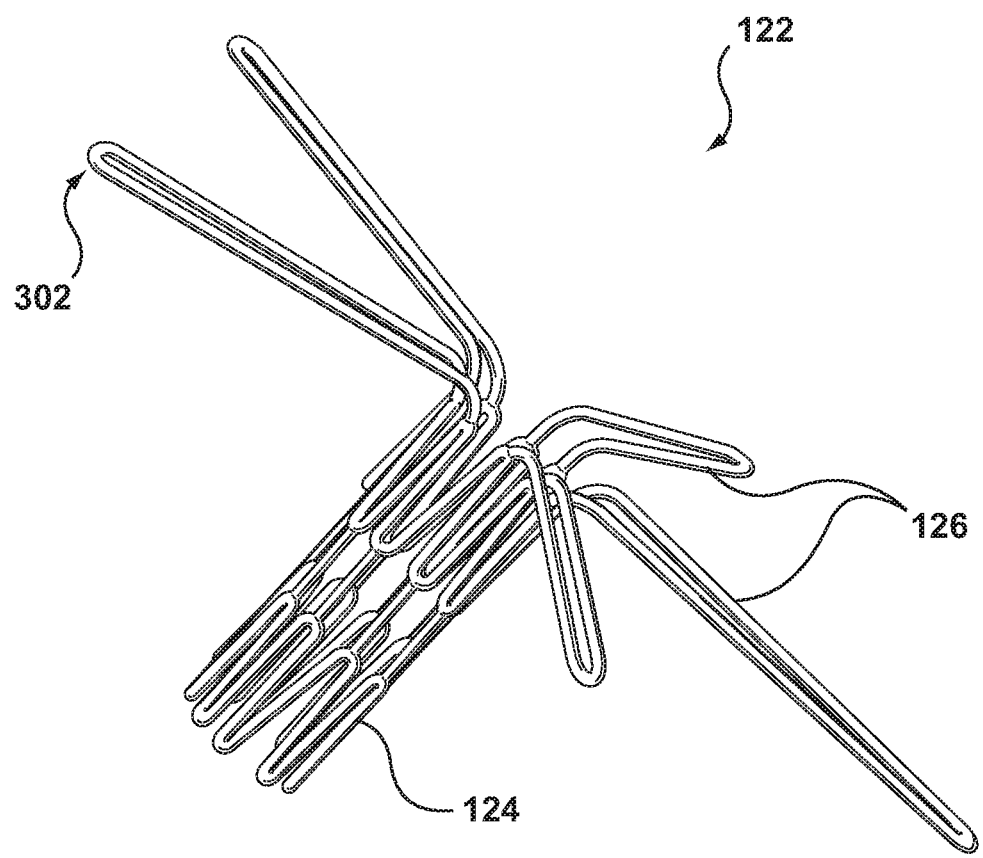

FIGS. 3A and 3B are images illustrating a coupling structure 122 according to one embodiment. The coupling structure 122 includes a tubular base portion 124, and a plurality of legs 126 that extend radially away from the base portion 124. In the illustrated embodiment, legs 126 are perpendicular or substantially perpendicular to a longitudinal axis of the tubular base portion 124. In one embodiment, coupling structure 122 is made from a shape memory material, such as Nitinol. FIGS. 3A and 3B show the coupling structure 122 in its natural state. In contrast, FIG. 1B shows the coupling structure 122 in a compressed state with the legs 126 bent toward the tubular base portion 124. In other embodiments, coupling structure 122 may be formed from a polymer, suture material, or other material. Each leg 126 includes an end portion 302 that forms a loop configured to be releasably coupled to a hook on the distal inflow end 212 of the prosthetic heart valve 214, as described in further detail below with reference to FIG. 4. In another embodiment, the distal end of the prosthetic heart valve 114 is an outflow end, and the coupling structure 122 is releasably coupled to the distal outflow end.

Figure 4:
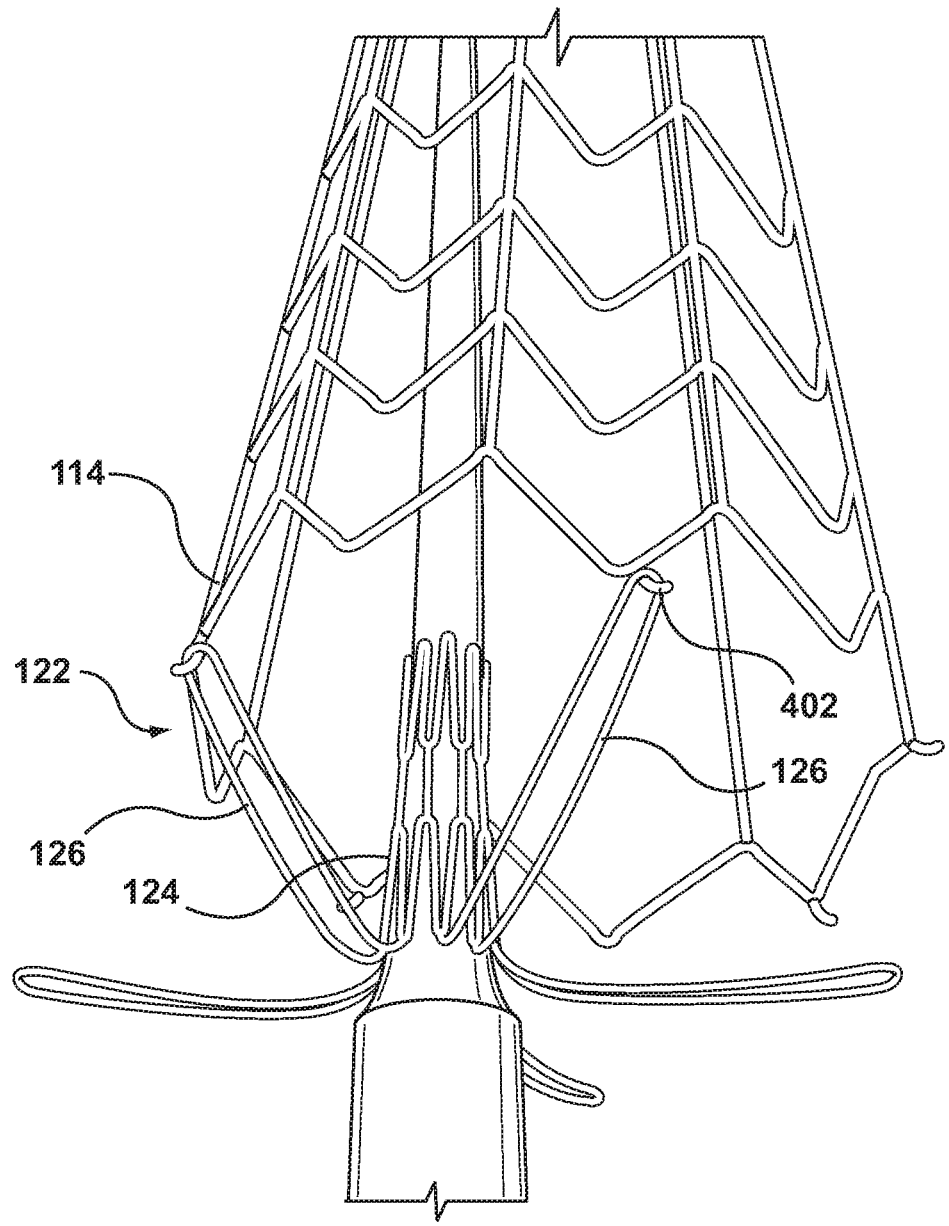
FIG. 4 is an image illustrating a coupling structure releasably coupled to a prosthetic heart valve according to one embodiment.

FIG. 4 is an image illustrating a coupling structure 122 releasably coupled to a prosthetic heart valve 114 according to one embodiment. Prosthetic heart valve 114 includes hooks 402 formed at the distal inflow end 112 of the valve 114. Each hook 402 is configured to be releasably coupled to one of the legs 126. As the prosthetic heart valve 114 expands, the legs 126 of the coupling structure 122 transition from the compressed state (shown in FIG. 1B), and the angle between each leg 126 and the longitudinal axis of the tubular base portion 124 increases. Eventually, the legs 126 reach an angle that causes the looped end portions 302 of the legs 126 to slide off their corresponding hooks 402, thereby releasing the prosthetic heart valve 114.

Figure 5A:
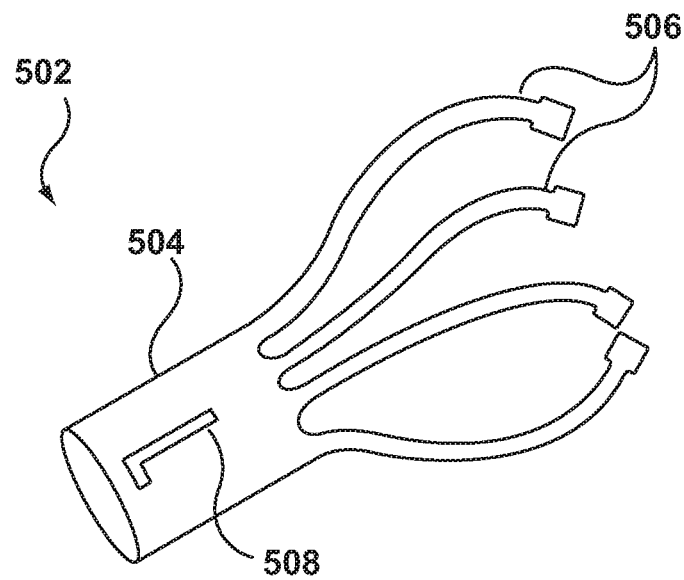
FIGS. 5A and 5B are diagrams illustrating a coupling structure according to another embodiment.
Figure 5B:
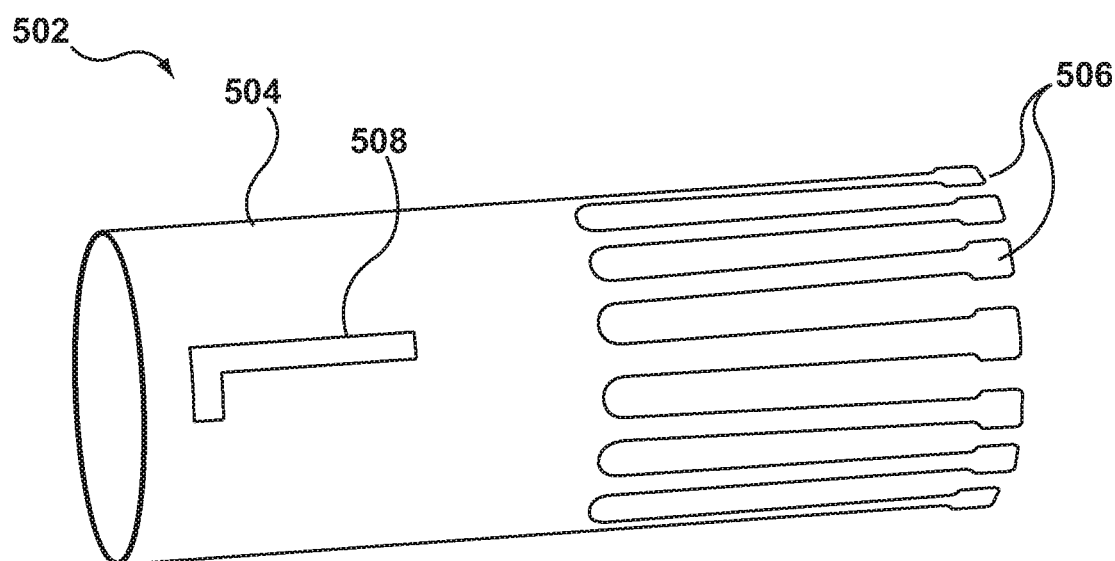

FIGS. 5A and 5B are diagrams illustrating a coupling structure 502 according to another embodiment. The coupling structure 502 is configured to be slidably attached to the nose cone 102, and the coupling structure 502 and the nose cone 102 are configured to slide in a longitudinal direction with respect to each other. In the illustrated embodiment, the coupling structure 502 includes a tubular base portion 504, and a plurality of legs 506 that extend away from the base portion 504. The distal end of the prosthetic heart valve 114 is configured to be releasably coupled to the legs 506 of the coupling structure 502. In one embodiment, coupling structure 502 is made from a shape memory material, such as Nitinol. FIG. 5A show the coupling structure 502 in its natural state, and FIG. 5B shows the coupling structure 502 in a compressed state. At least one slot 508 is formed in the tubular base portion 504 of the coupling structure 502. Although a single slot 508 is shown in FIGS. 5A and 5B, other embodiments may include multiple slots 508. Slot 508 is described in further detail below with reference to FIG. 6.

Figure 6:
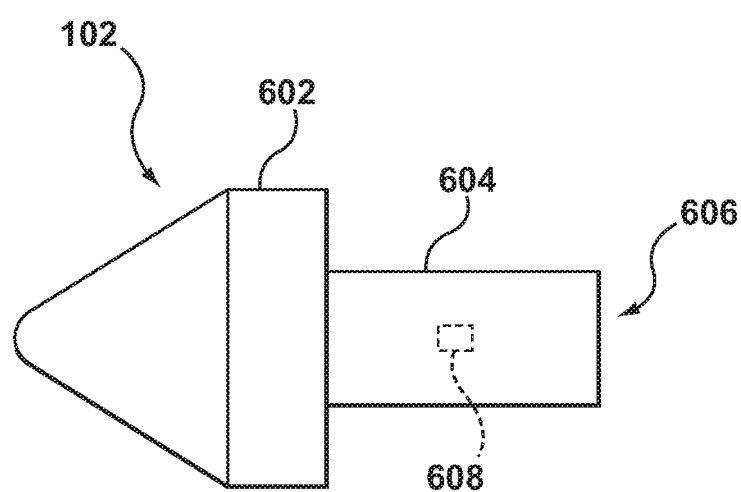
FIG. 6 is a diagram illustrating a nose cone compatible for use with the coupling structure shown in FIGS. 5A and 5B according to one embodiment.

FIG. 6 is a diagram illustrating a nose cone 102 compatible for use with the coupling structure 502 shown in FIGS. 5A and 5B according to one embodiment. Nose cone 102 includes a tip portion 602 and a tubular portion 604. The tubular portion 604 defines a lumen 606, which is configured to slidably receive the coupling structure 502. A feature 608 is formed within the lumen 606 on an inner surface of the tubular portion 604. Feature 608 is configured to be positioned within the slot 508 of the coupling structure 502, and guides the coupling structure 502 as it slides within the lumen 606. When coupling structure 502 is positioned within the tubular portion 604, the tubular portion 604 maintains the coupling structure 502 in the compressed state shown in FIG. 5B, which correspondingly compresses the distal end of the prosthetic heart valve 114. As coupling structure 502 slides outside of the tubular portion 604, the coupling structure 502 is allowed to gradually self expand towards its natural state shown in FIG. 5A, which correspondingly allows the distal end of the prosthetic heart valve 114 to self expand. In another embodiment, feature 608 is formed on the outer surface of the tubular portion 604, and coupling structure 502 is configured to longitudinally slide on the outer surface of the tubular portion 604. In one form of this embodiment, a separate actuator is provided in the delivery system 100 to control the coupling structure 502.

Coupling structure 502 according to one embodiment operates differently than coupling structure 122. For coupling structure 502, the prosthetic heart valve 114 is allowed to gradually self-expand by moving nose cone 102 in a first longitudinal direction (e.g., in a distal direction) via the handle device 112. As the nose cone 102 is moved in the first direction, the coupling structure 502 begins to slide outside of the lumen 606, resulting in the coupling structure 502 applying less compressive force to the prosthetic heart valve 114 and allowing the distal end of the valve 114 to self-expand. Proximal retraction of the sheath 104 and controlled expansion of the prosthetic heart valve 114 continues, with a continually increasing length of the prosthetic heart valve 114 being exposed and thus partially deployed, until the prosthetic heart valve 114 is fully deployed at the native heart valve. In one embodiment, continued movement of the nose cone 102 in the first direction causes the legs 506 to eventually slide off the distal end of the prosthetic heart valve 114 and thereby release the valve 114. Thus, the coupling structure 502 according to one embodiment is configured to be automatically released from the distal end of the prosthetic heart valve 114 when the prosthetic heart valve 114 expands beyond a threshold amount. After deployment, the nose cone 102 and the coupling structure 502 are pulled back through the deployed valve 114, and the delivery system 100 is removed from the patient.

For repositioning, nose cone 102 is moved in a second longitudinal direction (e.g., in a proximal direction) opposite the first direction via the handle device 112. As the nose cone 102 is moved in the second direction, the coupling structure 502 begins to slide back inside of the lumen 606, resulting in the coupling structure 502 applying more compressive force to the prosthetic heart valve 114, and causing a controlled contraction of the distal end of the valve 114. The sheath 104 is then advanced distally relative to the shaft assembly 110, and thus relative to the prosthetic heart valve 114. Distal movement of the sheath 104 continues until the prosthetic heart valve 114 is fully resheathed within the sheath 104. Once the prosthetic heart valve 114 is resheathed or recaptured, the system 100 can be repositioned relative to the implantation site, and the process repeated until the clinician is comfortable with the achieved positioning. Alternatively, the resheathed prosthetic heart valve 114 can be removed from the patient. The prosthetic heart valve 114 may also be repositioned without being completely resheathed.

Figure 7:
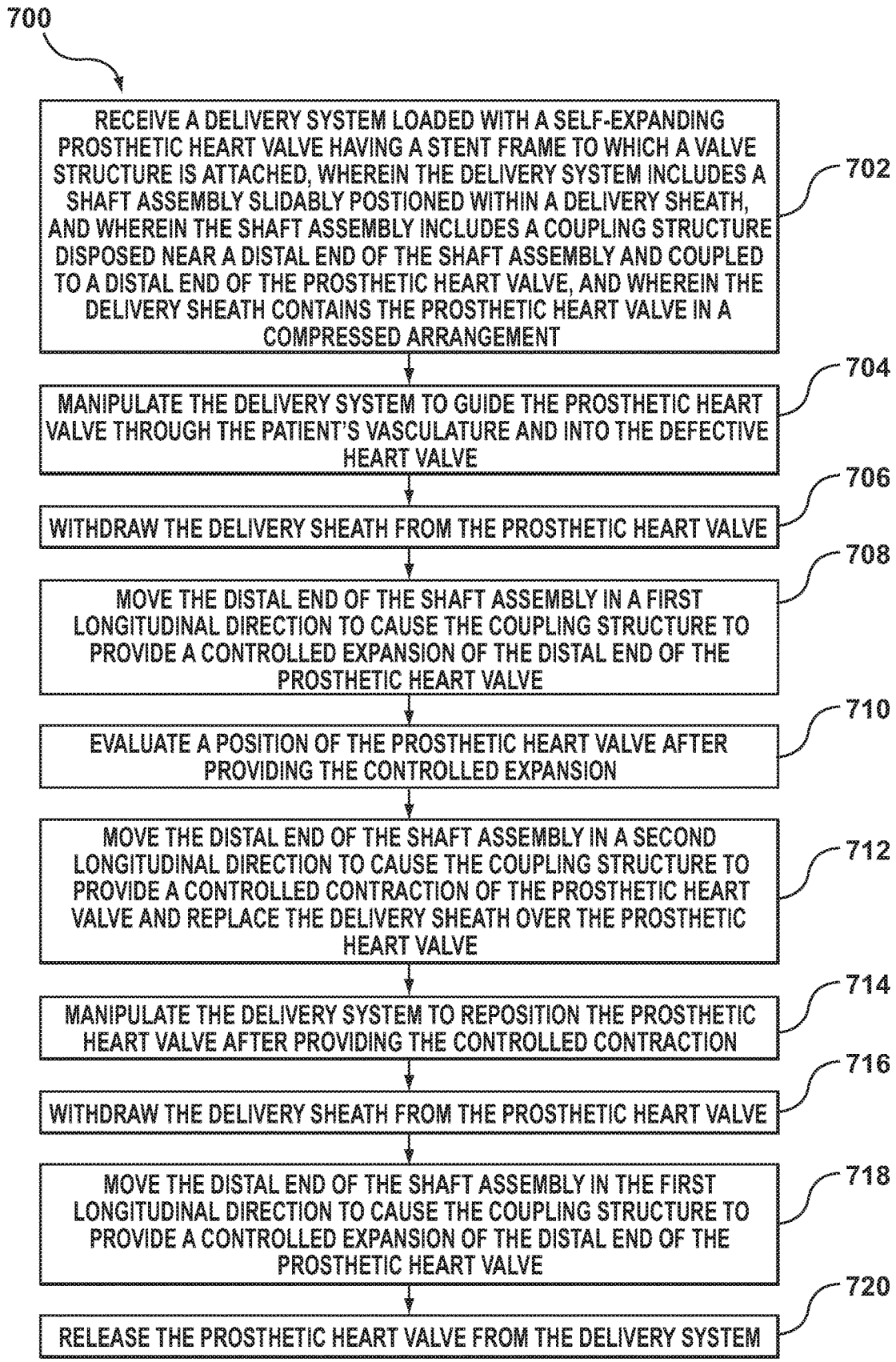
FIG. 7 is a flow diagram illustrating a method of performing a therapeutic procedure on a heart valve according to one embodiment.

FIG. 7 is a flow diagram illustrating a method 700 of performing a therapeutic procedure on a defective heart valve of a patient according to one embodiment. In one embodiment, delivery system 100 is configured to be used to perform method 700. At 702, a delivery system 100 loaded with a self-expanding prosthetic heart valve 114 having a stent frame 202 to which a valve structure 204 is attached is received, wherein the delivery system 100 includes a shaft assembly 110 slidably positioned within a delivery sheath 104, and wherein the shaft assembly 110 includes a coupling structure 122 or 502 disposed near a distal end of the shaft assembly 110 and coupled to a distal end of the prosthetic heart valve 114, and wherein the delivery sheath 104 contains the prosthetic heart valve 114 in a compressed arrangement.

At 704 in method 700, the delivery system 100 is manipulated to guide the prosthetic heart valve 114 through the patient's vasculature and into the defective heart valve. At 706, the delivery sheath 104 is withdrawn from the prosthetic heart valve 114. At 708, the distal end of the shaft assembly 110 is moved in a first longitudinal direction to cause the coupling structure 122 or 502 to provide a controlled expansion of the distal end of the prosthetic heart valve 114. At 710, a position of the prosthetic heart valve 114 is evaluated after providing the controlled expansion at 708. At 712, the distal end of the shaft assembly is moved in a second longitudinal direction to cause the coupling structure 122 or 502 to provide a controlled contraction of the prosthetic heart valve 114 and the delivery sheath 104 is replaced over the prosthetic heart valve 114. At 714, the delivery system 100 is manipulated to reposition the prosthetic heart valve 114 after providing the controlled contraction at 712. At 716, the delivery sheath 104 is again withdrawn from the prosthetic heart valve 114. At 718, the distal end of the shaft assembly 110 is moved in the first longitudinal direction again to cause the coupling structure 122 or 502 to again provide a controlled expansion of the distal end of the prosthetic heart valve 114. At 720, the prosthetic heart valve 114 is released from the delivery system 100.

Although the present disclosure has been described with reference to preferred embodiments, workers skilled in the art will recognize that changes can be made in form and detail without departing from the spirit and scope of the present disclosure.

What is claimed is:

1. A delivery system for a prosthetic heart valve comprising:
   a shaft assembly; and
   a coupling structure disposed near a distal end of the shaft assembly and configured to be coupled to the prosthetic heart valve, wherein the coupling structure self-expands from a compressed state to an expanded state via removal of compressive forces, wherein the coupling structure includes a base portion disposed near the distal end of the shaft assembly and a plurality of legs extending proximally from the base portion in the compressed state, wherein each of the legs includes an end portion to be coupled to a distal end of the prosthetic heart valve, and wherein the coupling structure provides a controlled gradual expansion of the prosthetic heart valve.

2. The delivery system of claim 1, wherein the coupling structure is configured to be automatically released from the prosthetic heart valve when the prosthetic heart valve expands beyond a threshold amount.

3. The delivery system of claim 1, wherein the coupling structure comprises a shape memory material.

4. The delivery system of claim 1, wherein the coupling structure comprises Nitinol.

5. The delivery system of claim 1, wherein the coupling structure is configured to be coupled to an inflow end of the prosthetic heart valve.

6. The delivery system of claim 1, wherein the coupling structure is configured to be coupled to an outflow end of the prosthetic heart valve.

7. The delivery system of claim 1, wherein the legs are angled away from a longitudinal axis of the base portion in the expanded state of the coupling structure.

8. The delivery system of claim 1, wherein the shaft assembly comprises a nose cone disposed at the distal end of the shaft assembly, and wherein the coupling structure is slidably attached to the nose cone.

9. The delivery system of claim 1, wherein the coupling structure provides the controlled gradual expansion and a controlled gradual contraction of the prosthetic heart valve based on longitudinal movement of the distal end of the shaft assembly that causes contraction and self-expansion of the coupling structure.

10. The delivery system of claim 1, further comprising:
    a sheath assembly defining a lumen sized to slidably receive the shaft assembly; and wherein the delivery system is configured to transition from a loaded state in which the sheath assembly encompasses the prosthetic heart valve to a deployed state in which the sheath assembly is withdrawn from the prosthetic heart valve.

11. A delivery system for a prosthetic heart valve comprising:
a shaft assembly; and
a coupling structure disposed near a distal end of the shaft assembly and configured to be coupled to the prosthetic heart valve, wherein the coupling structure self-expands from a compressed state to an expanded state via removal of compressive forces, wherein the coupling structure includes a base portion disposed near the distal end of the shaft assembly and a plurality of legs extending proximally from the base portion, wherein each of the legs includes an end portion to be coupled to a distal end of the prosthetic heart valve, and wherein the coupling structure provides a controlled gradual contraction of the prosthetic heart valve based on longitudinal movement of the shaft assembly.

12. The delivery system of claim 11, wherein the coupling structure is configured to be coupled to an inflow end of the prosthetic heart valve.

13. The delivery system of claim 11, wherein the coupling structure is configured to be coupled to an outflow end of the prosthetic heart valve.

14. The delivery system of claim 11, wherein the shaft assembly comprises a nose cone disposed at the distal end of the shaft assembly, and wherein the coupling structure is slidably attached to the nose cone.

15. The delivery system of claim 11, wherein the coupling structure provides a controlled gradual expansion and the controlled gradual contraction of the prosthetic heart valve based on longitudinal movement of the distal end of the shaft assembly.

16. The delivery system of claim 11, further comprising:
a sheath assembly defining a lumen sized to slidably receive the shaft assembly; and wherein the delivery system is configured to transition from a loaded state in which the sheath assembly encompasses the prosthetic heart valve to a deployed state in which the sheath assembly is withdrawn from the prosthetic heart valve.

17. The delivery system of claim 11, wherein the coupling structure is configured to be moved in a first direction to provide a controlled expansion of the prosthetic heart valve, and wherein the coupling structure is configured to be moved in a second direction opposite the first direction to provide a controlled contraction of the prosthetic heart valve.

18. The delivery system of claim 11, wherein the coupling structure comprises a shape memory material.

19. The delivery system of claim 11, wherein the legs are angled away from a longitudinal axis of the base portion in an expanded state of the coupling structure.

* * * * *